(12) United States Patent
Hillebrand et al.

(10) Patent No.: US 10,704,039 B2
(45) Date of Patent: Jul. 7, 2020

(54) DEVICE AND METHOD FOR EXTRACTING NUCLEIC ACIDS

(71) Applicant: AJ INNUSCREEN GMBH, Berlin (DE)

(72) Inventors: Timo Hillebrand, Hoppegarten (DE); Thorsten Stroh, Berlin (DE)

(73) Assignee: AJ Innuscreen GmbH, Berlin (DE)

( * ) Notice: Subject to any disclaimer, the term of this patent is extended or adjusted under 35 U.S.C. 154(b) by 0 days.

(21) Appl. No.: 15/568,474

(22) PCT Filed: Feb. 26, 2016

(86) PCT No.: PCT/EP2016/054179
§ 371 (c)(1),
(2) Date: Oct. 21, 2017

(87) PCT Pub. No.: WO2016/169678
PCT Pub. Date: Oct. 27, 2016

(65) Prior Publication Data
US 2018/0133710 A1    May 17, 2018

(30) Foreign Application Priority Data

Apr. 23, 2015 (DE) .................. 10 2015 207 481
Jun. 19, 2015 (DE) .................. 10 2015 211 393
Jun. 19, 2015 (DE) .................. 10 2015 211 394

(51) Int. Cl.
*B01L 3/02* (2006.01)
*C12N 15/10* (2006.01)
(Continued)

(52) U.S. Cl.
CPC ........ *C12N 15/1006* (2013.01); *B01L 3/0275* (2013.01); *C12N 15/1013* (2013.01);
(Continued)

(58) Field of Classification Search
CPC .............. B01L 3/0275; C12N 15/1006; C12N 15/1003; G01N 2200/0631
See application file for complete search history.

(56) References Cited

U.S. PATENT DOCUMENTS 5,171,537 A  *  12/1992  Wainwright  ..........  B01L 3/0275
422/514

FOREIGN PATENT DOCUMENTS

DE           37 17 211 A1     12/1988

OTHER PUBLICATIONS

Jun, Bong-Hyun et al. "Protein separation and identification using magnetic beads encoded with surface-enhanced Raman spectroscopy." Analytical Biochemistry (2009) 391 24-30. (Year: 2009).*

(Continued)

*Primary Examiner* — Christopher Adam Hixson
(74) *Attorney, Agent, or Firm* — Grüneberg and Myers PLLC

(57) ABSTRACT

Device and method for extraction of nucleic acids, comprising a hollow body, preferably a pipette tip, through which a liquid is passed, characterized in that a material with rough or structured surface is disposed in this hollow body in such a way that it can be circumcirculated by a liquid. After lysis of the sample and adjustment of necessary binding conditions for adsorption of the nucleic acids on the carrier material, the mixture, by means of pipetting processes, is repeatedly "pipetted along" the material for binding nucleic acids, introduced vertically in the pipette tip. The nucleic acids bind to the material. Thereupon washing buffers are likewise "pipetted along" the material for binding nucleic acids. Then a drying step is performed. Finally, the eluent is again repeatedly "pipetted along" the vertically disposed material for binding nucleic acids, and in the process the bound nucleic acid is detached. The nucleic acid is now available for necessary downstream application.

10 Claims, 1 Drawing Sheet

Figure 1:
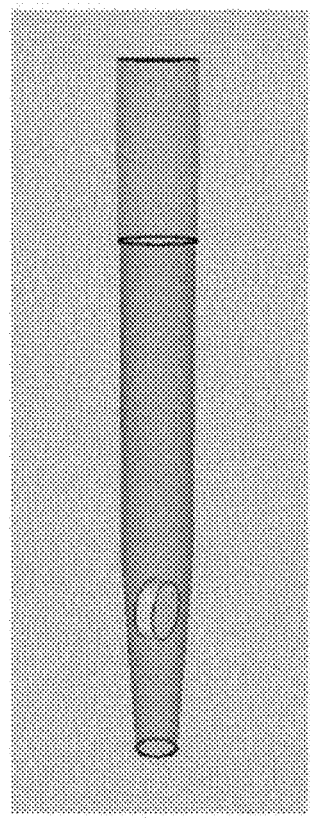

(51) Int. Cl.
　　　C12Q 1/6806　　(2018.01)
　　　G01N 1/40　　　(2006.01)
　　　G01N 35/10　　 (2006.01)

(52) U.S. Cl.
　　　CPC .......... *C12Q 1/6806* (2013.01); *G01N 1/405* (2013.01); *G01N 35/10* (2013.01); *B01L 2200/023* (2013.01); *B01L 2200/0631* (2013.01); *B01L 2200/0647* (2013.01); *B01L 2300/0854* (2013.01); *B01L 2300/16* (2013.01)

(56) References Cited

OTHER PUBLICATIONS

"Oberflaechenstrukturen." Technische Fakultaet der Christian-Albrechts-Universitaet obtained by the examiner on Mar. 16, 2019. (Year: 2019).*

Vogelstein et al. "Preparative and analytical purification of DNA from agarose" Proceedings of the National Academy of Sciences, vol. 76, No. 2; pp. 615-619: Feb. 1, 1979.

Akonni: "TruTip—Breaking the speed limit on ultra-rapid nucleic acid extraction," Nov. 16, 2010; Internet citation, https://web.archive.org/web/20130917232736/http:/www.akonni.com/docs/Tru-Tip%20Brochure.pdf—Date retrieved Nov. 20, 2017.

Chandler et al.; "Rapid, simple influenza RNA extraction from nasopharyngeal samples," J. Virological Methods; vol. 183, No. 1; pp. 8-13; Mar. 1, 2012.

Holmberg et al., "High-throughput, automated extraction of DNA and RNA from clinical samples using TruTip technology on common liquid handling robots," Journal of Visualized Experiments, No. 76; Jun. 11, 2013.

International Search Report mailed in PCT/EP2016/054179 dated Jun. 27, 2016, with English language translation.

Written Opinion of the International Searching Authority, mailed in PCT/EP2016/054179 dated Jun. 27, 2016, with English language translation.

International Preliminary Report on Patentability mailed in PCT/EP2016/054179 dated Oct. 24, 2017.

\* cited by examiner

DEVICE AND METHOD FOR EXTRACTING NUCLEIC ACIDS

CROSS-REFERENCE TO RELATED APPLICATIONS

The present application is a national stage entry under § 371 of PCT/EP2016/054179, filed on Feb. 26, 2016, which claims the benefit of priority of Germany Application Nos. 10 2015 207 481.1, filed on Apr. 23, 2015; 10 2015 211 393.0, filed on Jun. 19, 2015; and 10 2015 211 394.0, filed on Jun. 19, 2015; the contents of each of which are hereby incorporated by reference in their entirety.

The subject matter of the invention is a novel device with which nucleic acids can be isolated or purified rapidly and highly efficiently as well as quantitatively. The novel device for extraction of nucleic acids can be used both for manual extraction in the laboratory and under field conditions. Special advantages are disclosed in the context of automation of nucleic acid extractions.

Under traditional conditions, DNA is isolated from cells and tissues by digesting the starting materials containing nucleic acids under strongly denaturing and reducing conditions, sometimes also with use of protein-degrading enzymes, purifying the resulting nucleic acid fractions via phenol/chloroform extraction steps and obtaining the nucleic acids from the aqueous phase by means of dialysis or precipitation with ethanol (Sambrook, J., Fritsch, E. F. and Maniatis, T., 1989, CSH, "Molecular Cloning"). These "traditional methods" for isolation of nucleic acids from cells and especially from tissues are very time-consuming (sometimes longer than 48 hours), require highly complex apparatus and beyond that are also not feasible under field conditions. Moreover, such methods are hazardous to health to a not inconsiderable degree because of the chemicals used, such as phenol and chloroform.

The next generation of methods for isolation of nucleic acids is based on a method for preparative and analytical purification of DNA fragments from agarose gels, developed and described for the first time by Vogelstein and Gillespie (Proc. Natl. Acad. Sci. USA, 1979, 76, 615-619). The method combines the dissolution of the agarose containing the DNA bands to be isolated in a saturated solution of a chaotropic salt (NaI) with binding of the DNA on glass particles. The DNA fixed on the glass particles is then washed with a washing solution (20 mM Tris HCl [pH 7.2]; 200 mM NaCl; 2 mM EDTA; 50% v/v ethanol) and then detached from the carrier particles. Heretofore this method has undergone a series of modifications and at present is applied for different methods of extraction and purification of nucleic acids from different sources, ultimately becoming the basis for almost all commercially available kits for manual and also automated isolation of nucleic acids. Furthermore, numerous patents and publications are now known that relate to the basic principle of isolation of nucleic acids published for the first time by Vogelstein and Gillespie, some of them containing further advantages. These variants concern both the use of different mineral carrier materials and the type of buffers used for binding the nucleic acids. Examples include the binding of nucleic acids on mineral carriers in the presence of solutions of different chaotropic salts, in which finely ground glass powder (BIO 101, La Jolla, Calif.), diatomaceous earth (Sigma Co.) or even silica gels or silica suspensions or glass-fiber filters or mineral ores (DE 41 39 664 A1; U.S. Pat. No. 5,234,809; WO-A 95/34569 DE 4321904; DE 20207793) are used as carrier materials. All of these patents are based on the binding of nucleic acids on a mineral carrier material on the basis of glass or silicon in the presence of chaotropic salt solutions. In more recent patent specifications, it is disclosed that so-called anti-chaotropic salts as components of lysing/binding buffer systems can also be used very efficiently and successfully for adsorption of nucleic acids on the mineral materials known to and used by the person skilled in the art (EP 1135479). In summary, the prior art may therefore be described to the effect that nucleic acids bind to mineral materials in the presence of buffers that contain chaotropic or anti-chaotropic salts or even in the presence of buffers that contain mixtures of chaotropic and anti-chaotropic salts, and in this way can then also be isolated. In this connection, preferred variants are also known in which aliphatic alcohols are additionally used for mediation of binding. It is also known to the person skilled in the art that all common commercial products for isolation and purification of nucleic acids are based on this principle. The mineral carriers used for this purpose have the form of loose bulk material, the form of filter membranes or even the form of suspensions. Paramagnetic or magnetic particles are often used to perform automated extraction processes. Examples of these are silicate materials with a magnetic or paramagnetic core, or else iron oxide particles, the surface of which has been modified such that they have the functionalities necessary for binding nucleic acids. Modified pipette tips are used, especially so that automated extractions can be performed more easily. These are characterized in that they already contain the carrier materials (porous mineral carrier materials or porous anion exchangers, etc.) necessary for binding nucleic acids. Thus patent specification DE3717211 describes a pipette tip with a porous chromatography material for isolation of nucleic acids. Patent specification EP1951904 discloses a pipette tip consisting of an upper and lower part, between which a porous chromatographic carrier material is likewise disposed and which is intended for use in the automated isolation of nucleic acids. A modified pipette tip for extraction of nucleic acids is also disclosed in patent disclosure US2013/0078619. This pipette tip also contains a porous mineral carrier material (porous glass) for direct binding of nucleic acids. It is common to all of these modified pipette tips that they contain a porous chromatographic material (loose bulk material or solid porous bodies). These carrier materials are always disposed horizontally inside the pipette tips. The liquids to be processed flow through the porous material being used. The extraction process is based on the fact that, after lysis of the sample and adjustment of necessary binding conditions for adsorption of the nucleic acids on the carrier material, this mixture is drawn by means of a pipetting process through the porous carrier material. The nucleic acids bind to the carrier material. Thereupon washing buffers are pipetted through the carrier material. Then a drying step is performed (by frequently filling and emptying the pipette or by applying vacuum). Finally, the eluent is pipetted through the carrier material. In the process, the bound nucleic acid is detached from the carrier material. The use of pipette tips containing carrier material is intended to greatly simplify the extraction of nucleic acids (especially) by an automated process. Although these ideas are already relatively old in some cases (patent specification DE3717211 dates back to 22 May 1987), such a method has not become widely accepted. The reason for this lies in some fundamental problems:

1) The pipetting of highly viscous lysates containing nucleic acids functions to only a limited extent or leads to complete clogging of the chromatographic material. Thus extraction is not possible.

2) The pipetting of lysates through a porous material causes foaming. This is intensified with the increasing number of pipetting steps and it can likewise make the extraction process impossible.
3) The removal of alcoholic components from a porous material is difficult and in many cases is not satisfactorily solved.

Patent disclosure WO 01/05510 A1 also belongs to the prior art. It describes a hollow body containing magnetic particles. No information is provided about the surface properties of these magnetic particles. Nucleic acid binding by means of magnetic particles is normally achieved by means of smooth iron particles. Only the magnetic properties but not the surface properties played a role in the prior art.

The object underlying the invention was therefore to solve the known problems and to provide a simple and rapid method for extraction of nucleic acids by means of a modified pipette tip.

The object has been achieved according to the features of the claims. According to claim 1, a device for extraction of nucleic acids is provided that comprises a hollow body, through which a liquid is passed, wherein a material with rough or structured surface is disposed in this hollow body in such a way that it can be circumcirculated by a liquid. In a preferred embodiment, a pipette tip functions as the hollow body. The material with rough or structured surface has a size such that it cannot extend downward out of the pipette tip, and in this respect it differs from the magnetic particles described in the prior art (WO 01/05510 A1). Claims 2 to 6 describe preferred embodiments of the device. The invention also comprises an instrument according to the walk-away principle, which the device uses. Moreover, a method for isolation of nucleic acids by means of the device is described. This method is characterized by the following steps:

a) At least one substance that lowers the polarity of the aqueous solution or a means for binding nucleic acids on a solid phase is mixed with a lysed biological sample
b) This mixture from a) is drawn with a pipette tip, in which a rough or structured material according to one of claims 1 to 5 is disposed, and the pipette is filled and emptied several times, in the process of which the liquid moves along the material and the nucleic acids are precipitated on the rough or structured material—and in this way become bound on the solid phase
c) The pipette tip is removed from the sample
d) The pipette tip is immersed in a washing-buffer solution and the pipette is filled and emptied several times, in the process of which the liquid moves along the material.
e) The pipette tip is dried to remove the remaining alcohol from the washing buffer
f) The nucleic acid is detached with an elution buffer by filling and emptying the pipette several times with the elution buffer, in the process of which the elution buffer moves along the material.

Surprisingly, this can be accomplished with simple means. It has been discovered that a material for binding nucleic acids should be introduced not horizontally but instead vertically into a pipette tip, so that the liquid is able to flow without hindrance along one or both sides of the material for binding nucleic acids. In another embodiment, the pipette tip may also be filled with a particulate material for binding nucleic acids of such nature that sufficiently large voids exist within this material that a liquid likewise flows along this material and not through this material. In a further possible embodiment, a material with surface structure is disposed in a pipette tip. In this case, the liquid likewise flows along the "structures" of the material. All of these embodiments ultimately mean that the liquids used for isolation of nucleic acids move not through a chromatographic material but instead along a material for binding nucleic acids. This idea that nucleic acids can be isolated from liquid samples with the inventive means is based on a completely novel principle. This differs fundamentally from the known principles of isolation of nucleic acids on chromatographic carrier materials. It has been found that it is essential that the material used for binding the nucleic acids have a rough surface or that it be a material with surface structure that eliminates the smoothness because of the structure at the surface (this may be ordered or disordered). In conclusion, it is necessary that a two/three-dimensional structure on which nucleic acids can be adsorbed be formed by the introduced material inside the pipette tip. The binding of the nucleic acids appears to be based on the circumstance that, after the sample has been brought into contact with a rough surface, the nucleic acids contained in the sample precipitate on the rough surface, on a structured surface or on a two/three-dimensional network. This is accomplished by adding, for example, an alcohol that lowers the polarity of the environment and in this way reduces the solubility of the nucleic acid. Surprisingly, the "precipitation" of the nucleic acid on these described surfaces functions extremely efficiently with high yield and purity.

The core of the invention therefore consists in the fact that nucleic acids in free form or liberated by lysis are present in an aqueous environment, the polarity of which is adjusted in such a way by means of organic substances that the solubility of the nucleic acid is reduced, after which this aqueous environment is drawn into the inventive pipette tip, so that the nucleic acid is then moved along (which can be achieved by pipetting several times) the material/network introduced into the pipette tip and precipitates on the surface of the material/network, after which the precipitated DNA is detached from the surface once again and becomes available. Optionally, the nucleic acid precipitated on the surface may also be washed and then detached after washing steps.

The practical process of extraction by means of the inventive method is therefore based on the following steps. After preparation of a sample containing nucleic acid in an aqueous form, the conditions necessary for precipitation of the nucleic acids are adjusted in such a way that the nucleic acid is able to precipitate on the material introduced into the pipette tip. By means of pipetting processes the mixture is "pipetted along" material for binding nucleic acids, introduced vertically in the pipette tip. The nucleic acids precipitate on the material. As an option, washing buffers may then likewise be "pipetted along" the material for binding nucleic acids. Then a drying step is performed (e.g. by frequently filling and emptying the pipette). Finally, the eluent is again repeatedly "pipetted along" the vertically disposed material for binding nucleic acids, and in the process the bound nucleic acid is detached. The nucleic acid is now available for necessary downstream application. The method is extremely fast and easy to perform, and it permits isolation of nucleic acids in an extremely high yield and purity. No problems exist with viscous solutions, nor do problems with the removal of alcoholic components or with extreme foaming, as is the case during the use of all horizontally disposed porous carrier materials or of pipette tips filled with a porous chromatographic material. The method is universally usable and can be performed in an automated process as well as manually. It is most ideally suitable for the use of automated nucleic acid extraction, since the necessary steps for binding nucleic acids, for washing the bound nucleic acids and for detachment of the nucleic acids are now merely multiple pipetting steps. In the process, the inventive pipette tip circumvents the known disadvantages of the prior art resulting from the previous structural arrangement or filling of pipette tips with porous chromatographic materials.

The materials to be used for binding nucleic acids, introduced vertically into the pipette tip, may be extremely different. Besides mineral materials, it is also possible to use modified plastic materials, the surface of which is not smooth but instead is rough or structured. They also include so-called composite materials, mixtures of polymers and, for example, organic components, and also inorganic components as well as composite materials. What is important is merely the provision of a roughened or structured surface (not a smooth surface) or the introduction, into the pipette tip, of material that leads to formation of a two/three-dimensional network, in which case the nucleic acids then precipitate on this structure. The architecture of the material is likewise not limitative (round, rectangular, etc.). This material may also comprise several materials (e.g. several granulated materials). In simple embodiments, even one screw introduced into the pipette tip may be used alone for isolation of nucleic acids.

What is important is merely that the material be introduced into a pipette tip where it can be circumcirculated by a liquid at any time without the requirement that the liquid pass through the introduced material. It is also possible to use a pipette tip in which the binding material (made from an injection-molded part) is already disposed and no longer has to be introduced into the tip. The use of rough, magnetic material is also advantageous. Such a material is known as granulated material under the brand name TECACOPM®.

The term "rough surface" is to be understood as a surface that is obviously not smooth to the touch or to the eye. However, it may also be a surface that has a structure (e.g. grooves). Because of this structure, the smoothness of the surface is eliminated, even if the structure, i.e. the grooves, may itself be smooth. According to the invention, such surfaces are referred to as "structured surfaces". If it is not obvious to the eye or to the touch whether a surface is smooth or rough, a test in which a laser beam is directed onto this surface may be performed. If the surface is smooth, the laser will be reflected only in the primary direction at the surface. In the case of rough surfaces, scattering takes place in all spatial directions. Such a test has been described on the website of Kiel University (http://www.tf.uni-kiel.de/matwis/amat/semitech_en/kap_3/illustr/oberflaechenstruktur.pdf.)

The invention will be explained in more detail hereinafter on the basis of exemplary embodiments. These exemplary embodiments do not represent any limitation of the invention.

EXEMPLARY EMBODIMENTS

Example 1: Manual Extraction of Nucleic Acid from NIH 3T3 Cells by Means of the Inventive Method Using a Modified Pipette Tip In a 1-mL pipette tip (Sarstedt Co.), a polyethylene disk was fixed vertically in the last third. $5 \times 10^5$ NIH 3T3 cells were used. The extraction chemistry used for isolation of the nucleic acids was obtained in part from the commercial extraction kit known as innuPREP Blood DNA Kit/IPC16X (Analytik Jena AG). Using a lysis buffer (Lysis Solution CBV) as well as Proteinase K, the cells were lysed at 60° C. for 15 minutes. Lysis was carried out in a 2.0-mL reaction vessel. After lysis, 400 µL isopropanol was added to the mixture. Then the modified pipette tip was used, and the mixture was filled into and emptied from a pipette 20 times. Thereafter 3 further 2-mL reaction vessels were filled with the alcoholic washing buffers (Washing Solution LS, 80% ethanol, 80% ethanol). The pipette tip was them immersed successively in the respective washing buffers and the pipette was filled and emptied 5 times in each case. After the last washing step, the tip was dried, so that the remaining ethanol was removed. The bound nucleic acid was eluted with 100 µL Elution Buffer. It was again introduced into a 2-mL reaction vessel. This was emptied and refilled 30 times by pipette. After removal of the pipette tip, the isolated nucleic acid was contained in the reaction vessel. The method is extremely easy and fast.

The isolated nucleic acid was detected by means of spectrophotometric measurement.

Results of Spectrophotometric Measurement

| Sample | Concentration (ng/µL) | Yield (µg) | Ratio $A_{260}:A_{280}$ | Ratio $A_{260}:A_{230}$ |
|---|---|---|---|---|
| 1 approx. $1 \times 10^5$ NIH 3T3 cells | 264 | 26.4 | 1.95 | 2.10 |
| 2 approx. $1 \times 10^5$ NIH 3T3 cells | 228 | 22.8 | 1.94 | 2.09 |
| 3 approx. $1 \times 10^5$ NIH 3T3 cells | 222 | 22.2 | 1.97 | 2.11 |

As the results show, it is possible with the inventive means, solely by using standard extraction chemistry and a few pipetting steps with a standard pipette, to bind and to isolate nucleic acids. It has been found that the yields are extremely high.

Example 2: Automated Extraction of Nucleic Acid from NIH 3T3 Cells by Means of the Inventive Method and Using a Modified Pipette Tip as Well as Using a Commercially Available Automated Extraction System Automated extraction was performed with the InnuPure C16 automated extraction system (Analytik Jena AG). This automated extraction system is based on extraction of nucleic acids by magnetic particles.

In order to perform a nucleic acid extraction according to the inventive method, the pipette tips used for the automated extraction system were modified to correspond to the inventive means. A disk made from a roughened polymer was introduced vertically into the pipette tips, in the bottom third, without closing the lumen, so that the pipetting function of the pipette tips was preserved. Roughened disks of various materials were used for this purpose. In each case, $5 \times 10^5$ NIH 3T3 cells were used for the extraction of nucleic acids. The extraction chemistry used for isolation of the nucleic acids was obtained in part from the commercial extraction kit known as innuPREP Blood DNA Kit/IPC16X (Analytik Jena AG). Using a lysis buffer (Lysis Solution CBV) as well as Proteinase K, the cells were lysed at 60° C. for 15 minutes in a 2.0-mL reaction vessel.

Subsequently, the automated method of the Innupure C16 was used for purification of the nucleic acids. The solutions needed for extraction were present in a prefilled deep well plate. The lysates described hereinabove were introduced into cavities filled with 400 µL isopropanol. Thereupon this solution was thoroughly mixed by means of the pipette tip in such a way that the solution flowed along the sides of the disk introduced into the tip. 100 repetitions were performed.

Then thorough mixing was performed 5 times each successively in three further cavities, which contained the alcoholic washing buffers (Washing Solution LS, 80 ethanol, 80% ethanol).

Following the last washing step, the inventive tip and the disk contained therein were dried by pipetting air 200 times, and in this way the remaining ethanol was removed. The nucleic acids were eluted by 120 cycles of thorough mixing with 100 µL Elution Buffer, which had been previously adjusted to a temperature of 50° C. by the instrument. The total volume of Elution Buffer was 200 µL.

The method is extremely easy and fast, and it shows that commercially available automated extraction systems can be used to perform the inventive method with the inventive means corresponding thereto. It is much less time-consuming than extraction based on magnetic particles. The isolated nucleic acid was detected by means of spectrophotometric measurement.

Results of the Spectrophotometric Measurement:

| Material | Concentration (ng/µL) | Yield (µg) | Ratio $A_{260}:A_{280}$ | Ratio $A_{260}:A_{230}$ |
| --- | --- | --- | --- | --- |
| Polylactic acid | | | | |
| 1 | 31.67 | 6.34 | 1.95 | 2.19 |
| 2 | 25.18 | 5.04 | 1.8 | 2.11 |
| BioFila linen | | | | |
| 3 | 56.23 | 11.25 | 1.87 | 2.17 |
| 4 | 67.63 | 13.52 | 1.85 | 2.18 |
| Polycarbonate | | | | |
| 5 | 38.12 | 7.62 | 1.79 | 2.13 |
| 6 | 21.9 | 4.38 | 2.14 | 2.36 |
| Polyhydroxyalkanoate | | | | |
| 7 | 30.33 | 6.06 | 1.89 | 2.02 |
| 8 | 42.49 | 8.5 | 1.85 | 2.13 |
| Styrene-acrylonitrile | | | | |
| 9 | 27.26 | 5.45 | 1.9 | 1.87 |
| 10 | 32.03 | 6.4 | 1.76 | 2.13 |
| Polystyrene | | | | |
| 11 | 28.85 | 5.77 | 1.83 | 2.02 |
| 12 | 4.75 | 0.95 | 1.42 | 1.3 |
| Polyethylene | | | | |
| 13 | 25.43 | 5.09 | 1.76 | 1.53 |
| 14 | 48.43 | 9.96 | 1.85 | 1.82 |

Figure 2:
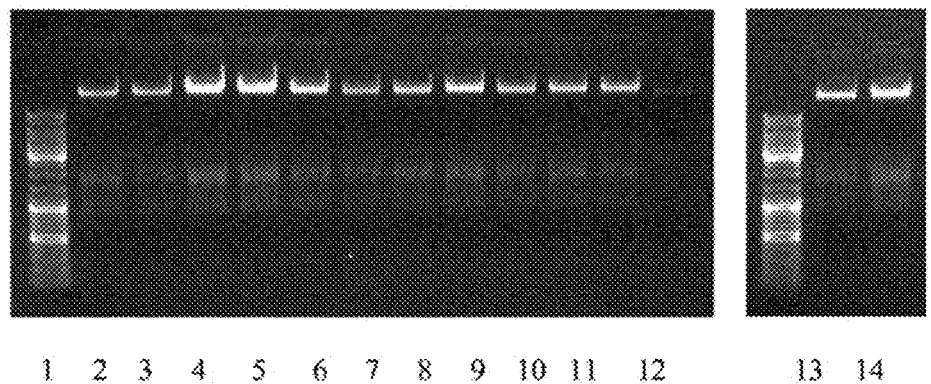

FIG. 2 shows a gel-electrophoretic analysis of the isolated nucleic acids.

It illustrates the nucleic acid isolated by means of the inventive method and separated electrophoretically in an 0.8% agarose gel. The samples were applied from left to right, beginning with sample 1.

As the results show, it is possible with the inventive means, which may consist of different polymers, solely by using standard extraction chemistry and a few pipetting steps with a standard pipetting platform, to bind and to isolate nucleic acids. It has been found that the yields are extremely high.

Example 3: Automated Extraction of Nucleic Acid from Blood Cells by Means of the Inventive Method and Using Pipette Tips that Contain Different Materials for Isolation of Nucleic Acids as Well as Using a Commercially Available Automated Extraction System Automated extraction was performed with the InnuPure C16 automated extraction system (Analytik Jena AG). This automated extraction system is based on extraction of nucleic acids by magnetic particles.

In order to perform a nucleic acid extraction according to the inventive method, the pipette tips used for the automated extraction system were modified to correspond to the inventive means. Three different tips were used:

Type 1: Pipette tip containing a three-dimensional network of metal in the form of some cuttings from a commercially available, so-called metal cleaning sponge (stainless-steel spirals) was used. This material was stuffed into the pipette tip. It produces a three-dimensional network, along which the solution is pipetted.

Type 2: Pipette tip with two oppositely inserted galvanized wood screws (these represent a structured surface according to the description)

Type 3: Pipette tip with 4 plastic granules, the surface of which was roughened beforehand. These plastic granules of polyethylene represent a material with a rough surface according to the description. Ferromagnetic material with polypropylene.

In each case, blood cells isolated beforehand from 2 mL whole blood were used for the extraction of nucleic acids. The blood cells were resuspended in 200 µL PBS. The extraction chemistry used for isolation of the nucleic acids was obtained in part from the commercial extraction kit known as innuPREP Blood DNA Kit/IPC 16 (Analytik Jena AG). The entire extraction process was carried out in automated manner using the Innupure C16 instrument (Analytik Jena AG). The instrument is based on a walk-away principle. For this purpose, a deep well plate is prefilled with the needed reagents. The pipette tip (with the inventive modifications) is then introduced successively into the individual cavities and the respective solutions are drawn into the pipette tip by filling and emptying the pipette, thus being pipetted along the material contained in the pipette tip.

First of all, the cell suspension was transferred into the first cavity of the prefilled deep well plate. This cavity contained the lysis buffer as well as Proteinase K. Lysis was carried out by filling the lysate into and emptying it from the pipette multiple times via the inventive pipette tip. After lysis, the lysate was transferred into the next cavity. This cavity contained isopropanol. Once again, the pipette was filled and emptied multiple times and thus the liquid was drawn continuously into the interior of the pipette tip, in the process being passed along the material disposed in the pipette tip. In this step, the nucleic acid binds to the material. After this step, the pipette tip was moved into the next cavities. These contained alcoholic washing buffers. In this way the bound nucleic acid was washed once again by multiple pipetting processes. After the pipette tip had been dried, it was moved into a further cavity containing water. The nucleic acid was detached from the material and finally obtained in dissolved form by filling and emptying the pipette. In this way the entire extraction process was carried out in completely automated manner.

The method is extremely easy and fast, and it shows that commercially available automated extraction systems can be used to perform the inventive method with the inventive means corresponding thereto. It is much less time-consuming than extraction based on magnetic particles.

The isolated nucleic acid was detected by means of spectrophotometric measurement.

Results of the Spectrophotometric Measurement:

| Material | Concentration (ng/µL) | Yield (µg) | Ratio $A_{260}:A_{280}$ | Ratio $A_{260}:A_{230}$ |
|---|---|---|---|---|
| Tip with three-dimensional structure (stainless-steel wool) | | | | |
| 1 | 62 | 24.8 | 1.8 | 1.9 |
| 2 | 70 | 28.0 | 1.8 | 1.9 |
| 3 | 75 | 30.0 | 1.8 | 2.0 |
| Tip with galvanized screws | | | | |
| 1 | 38 | 15.2 | 1.7 | 1.6 |
| 2 | 42 | 18.0 | 1.8 | 1.8 |
| 3 | 45 | | 1.7 | 1.7 |
| Tip with rough plastic granules of PE | | | | |
| 1 | 80 | 32.0 | 1.8 | 2.2 |
| 2 | 94 | 37.6 | 1.8 | 2.2 |
| 3 | 102 | 40.8 | 1.8 | 2.2 |

FIG. 1: shows an exemplary representation of the disk of a polymer material for binding nucleic acids, introduced vertically into the hollow body; it illustrates an exemplary embodiment of the inventive means that can be used for extraction of nucleic acids according to the inventive method.

The invention claimed is:

1. A device for extraction of nucleic acid, the device comprising:
    a hollow body, through which a liquid can be passed, wherein
    a material with rough or structured surface is disposed in said hollow body in such a way that it can be circum-circulated by a liquid, wherein said material is in the form of a screw.

2. The device according to claim 1, wherein
    the hollow body is a pipette tip and the material has a size that prevents it from escaping from the pipette tip.

3. The device according to claim 1, wherein
    the material is a rough or structured polymer material, a composite material with rough surface or a material produced by 3D printing.

4. The device according to claim 1, wherein
    the material with rough or structured surface is a material with non-smooth metal, plastic or rubber surface.

5. The device according to claim 1, wherein
    the hollow body is a pipette tip, which is roughened on the inside wall or on the inside wall of which the introduced material is immobilized.

6. An instrument for automated extraction of nucleic acid, the instrument comprising:
    at least one device according to claim 1.

7. An instrument according to claim 6, which
    is an automated pipetting system or an automated extraction system.

8. A method for automated extraction of nucleic acid, the method comprising:
    a) mixing at least one substance that lowers the polarity of the aqueous solution or a composition that binds nucleic acid on a solid phase with a lysed biological sample;
    b) drawing a mixture from said a) mixing with a pipette tip, in which a rough or structured material is disposed, and the pipette is filled and emptied several times, in the process of which the liquid moves along the material and the nucleic acid are precipitated on the rough or structured material;
    c) removing the pipette tip from the sample;
    d) immersing the pipette tip in a washing-buffer solution and the pipette is filled and emptied several times, in the process of which the liquid moves along the material;
    e) drying the pipette tip to remove the remaining at least one substance what lowers the polarity of the aqueous solution from the washing buffer; and
    f) detaching the nucleic acid with an elution buffer by filling and emptying the pipette several times with the elution buffer, in the process of which the elution buffer moves along the material.

9. The method according to claim 8, wherein
    the substance for lowering the polarity of the aqueous solution is at least one organic solvent.

10. The method according to claim 8, wherein said pipette is comprised within an automated pipetting system or an automated extraction system.

* * * * *